United States Patent [19]

Stringer et al.

[11] Patent Number: 4,554,287

[45] Date of Patent: Nov. 19, 1985

[54] ANTIHYPERTENSIVE 7-[2-(DIALKYLAMINO)ETHYL]-4-HYDROXY-1,3-BENZIMIDAZOL-2-ONES

[75] Inventors: Orum D. Stringer, Philadelphia; Joseph Weinstock, Phoenixville, both of Pa.

[73] Assignee: Smithkline Beckman Corporation, Philadelphia, Pa.

[21] Appl. No.: 649,465

[22] Filed: Sep. 12, 1984

[51] Int. Cl.$^4$ ................. A61K 31/415; C07D 235/26
[52] U.S. Cl. .................................. 514/387; 548/305; 564/51
[58] Field of Search .................. 548/305; 514/387

[56] References Cited

U.S. PATENT DOCUMENTS

| | | | |
|---|---|---|---|
| 4,070,478 | 1/1978 | Talaty et al. | 548/305 X |
| 4,314,944 | 2/1982 | Huffman et al. | 548/486 |
| 4,367,235 | 1/1983 | Ross et al. | 548/305 X |

Primary Examiner—Richard A. Schwartz
Attorney, Agent, or Firm—William H. Edgerton; Richard D. Foggio; Alan D. Lourie

[57] ABSTRACT

7-[2-Dialkylamino)ethyl]-4-hydroxy-1,3-benzimidazol-2-ones are prepared by oxidative cyclization of a urea, followed by removal of protective groups. The compounds are D$_2$-agonists and, thereby, have anti-hypertensive activity. A species of the group is 7[2-N,N-di-n-propylamino)ethyl]-4-hydroxyl-1,3-benzimidazol-2-one.

10 Claims, No Drawings

ANTIHYPERTENSIVE 7-[2-(DIALKYLAMINO)ETHYL]-4-HYDROXY-1,3-BENZIMIDAZOL-2-ONES

This invention relates to new chemical compounds which are 7-[2-(dialkylamino)ethyl]-4-hydroxy-1,3-benzimidazol-2-ones. Pharmaceutical compositions, which use these compounds as active ingredients, induce dopaminergic or, more specifically, $D_2$-agonist activity which is useful for treating hypertension.

DESCRIPTION OF THE PRIOR ART

U.S. Pat. No. 4,314,944 discloses a series of 4-aminoalkyl-7-hydroxy-2(3H)-indolones which have renal dopaminergic activity. The structures of the compounds of the present invention have a nucleus which differs from that of the indolones by having another aza member.

DESCRIPTION OF THE INVENTION

The compounds of this invention are illustrated by the following structural formula:

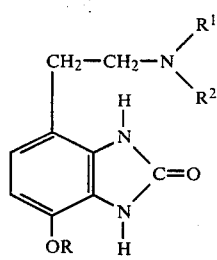

in which:
R is hydrogen or methyl, and
$R^1$ and $R^2$ are, each, $C_{1-6}$-alkyl, benzyl, phenethyl, methoxyphenethyl or hydroxyphenethyl.

The compounds of formula I in which $R^1$ and $R^2$ are both n-propyl or are n-propyl, 4-hydroxyphenethyl, with R being hydrogen in each instance, are preferred.

The pharmaceutically acceptable acid addition salts which have the utility of the free bases of formula I are part of this invention. These are prepared by methods known to the art and are formed with both nontoxic, inorganic or organic acids, for example: maleic, fumaric, benzoic, ascorbic, pamoic, succinic, bismethylenesalicylic, methane sulfonic, ethane disulfonic, acetic, propionic, tartaric, salicylic, citric, gluconic, stearic, palmitic, itaconic, glycolic, benzenesulfonic, hydrochloric, hydrobromic, sulfuric, phosphoric or nitric acids. The hydrohalic and, especially, methane sulfonic acid salts are conveniently used.

Also included in this invention are the O-$C_{2-6}$-alkanoyl derivatives of the compounds of formula I. These are prepared by O-acylation of any compound of formula I which has a hydroxy group in its structure using a lower alkanoyl halide or anhydride, optionally in the presence of a base.

The compounds of formula I are prepared by the following reaction sequence:

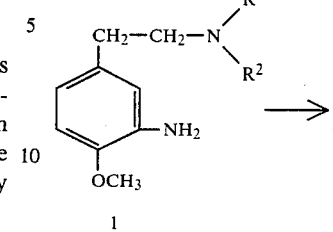

1

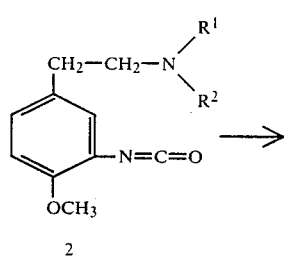

2

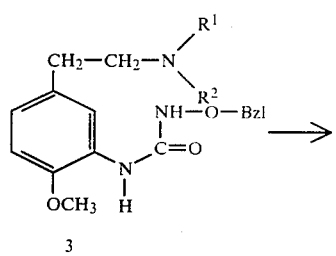

3

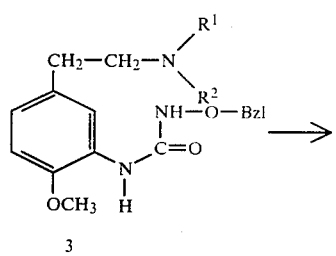

4

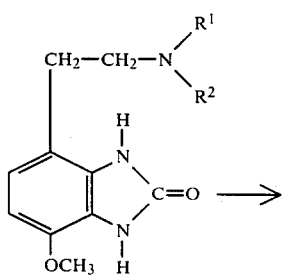

5

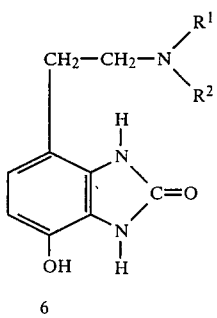

in which R[1] and R[2] are as defined above. Bzl is benzyl or another protective alkyl group.

The compounds of this invention are prepared by the novel synthetic sequence presented above. A 3-amino-4-methoxyphenethylamine (1) is reacted with phosgene to form the 3-isocyanate (2). This is reacted with a O-lower alkyl hydroxylamine to form a substituted urea (3) which is then oxidatively cyclized, such as in the presence of lead tetraacetate. The N-benzyloxy group is removed from intermediate (4) using catalytic hydrogenation to give the 4-methoxy-7-[2-(dialkylamino)ethyl]-1,3-benzimidazol-2-ones of formula 5. The ether derivatives have $D_2$-agonist activity but are less potent than are their parent hydroxy compounds.

The final step of the sequence involves the dealkylation of the O-protected ether products of structure 5. Optional dealkylation at position 4 as well as at any other protected groups, such as a 4-alkoxy substituent on the aromatic ring (when $R_1$ or $R_2$=phenethyl), is accomplished by the reaction of compound 5 with refluxing 48% hydrogen bromide, boron tribromide or boron trichloride in the cold, hydriodic acid, aluminum chloride, pyridine hydrochloride or other dealkylation-splitting agents. The temperature range can vary from −15° to reflux temperatures depending on the nature of the protecting groups and the dealkylating agent as known to the art. The reaction is usually complete in from 1–5 hours. The desired product is isolated as the base or as an acid addition salt by conventional chemical methods.

The overall reaction sequence is illustrated in more detail in Example 1 hereafter.

The compounds of this invention have utility, as dopamine agonists, in the treatment of disorders of the cardiovascular system, especially to treat hypertension, to treat angina pectoris, to treat the symptoms of congestive heart failure or to improve kidney vasodilation.

More specifically, the compounds of this invention, especially 7-[2-(N,N-di-n-propylamino)ethyl]-4-hydroxy-1,3-benzimidazol-2-one as the hydrobromide salt, have proved to be peripheral $D_2$-agonists. Otherwise speaking, the main locus of action is at the presynaptic dopaminergic receptors or sympathetic nerve terminals which may also be called "$D_2$-receptors." Activation of the $D_2$-receptors on the sympathetic nerve terminals inhibits the release of norepinephrine, thereby inhibiting the increases in cardiac rate and the peripheral vasoconstriction resulting from stimulation of the sympathetic nervous system. These are beneficial cardiovascular actions in those conditions involving excessive or inappropriate levels of sympathetic nervous system stimulation.

In the perfused rabbit ear artery test for $D_2$-agonist activity [J. P. Hieble et al., Arch. Pharmacol. 309 217 (1979)], the above-named compound had an $EC_{50}$ in the range of 9 nM. In the same test system, N,N-di-n-propyldopamine had an $EC_{50}$ of from 50–60 nM; dopamine, 40 nM.

The pharmaceutical compositions of this invention have pharmacodynamic activity within the cardiovascular system, for example renal vasodilatation, the ability to correct hemodynamic imbalance, anti-anginal activity, anti-hypertensive activity and bradycardia. The compositions are prepared in conventional dosage unit forms by incorporating a compound of formula I, or a pharmaceutically acceptable acid addition salt or ester thereof, with a pharmaceutical carrier, according to accepted pharmacy procedures, in a nontoxic quantity of the active ingredient which is sufficient to produce the desired pharmacodynamic activity in an animal or human patient in need thereof. Preferably, the compositions will contain the active ingredient in an active but nontoxic quantity which is selected from the range of about 10 mg to about 300 mg, preferably from the range of 50–150 mg, of active ingredient, as the base, per dosage unit. This quantity depends on the relative potency of the base compound compared with that of the prototypic species, 7-[2-(N,N-di-n-propylamino)ethyl-4-hydroxy-1,3-benzimidazol-2-one, as well as on the specific biological activity desired, the route of administration, that is, whether oral or parenteral, and the condition and size of the patient.

The pharmaceutical carrier employed for the dosage units is, for example, either a solid or liquid. Exemplary of solid carriers are lactose, terra alba, sucrose, talc, gelatin, agar, pectin, acacia, magnesium stearate or stearic acid. Exemplary of liquid carriers are isotonic saline for parenteral use or syrup, peanut oil, olive oil or water for soft gelatin capsules. Similarly, the carrier or diluent may include any time delay material well known to the art, such as cellulose esters or ethers and glyceryl esters alone or admixed with a wax. Sustained release products as well as prodrug derivatives which may be gradually metabolized to the active parent can be employed to prolong the unique biological activity of the compounds of this invention or to attack receptors at a specific location.

A wide variety of pharmaceutical forms are employed. Thus, if a solid carrier for oral or rectal administration is used, the mixed preparation is optionally tableted, placed in a hard gelatin capsule in powder or sustained release pellet form or incorporated in a dermal patch, a suppository or a troche. The amount of solid carrier will vary widely but, preferably, will be from about 25 mg to about 1 g. If a liquid carrier is used, the preparation will be in the form of a syrup, emulsion, soft gelatin capsule, sterile injectable liquid of an ampul or multidose vial, or an aqueous or nonaqueous liquid suspension for oral administration.

Advantageously, doses selected from the dosage unit ranges given above will be administered to the patient in need of treatment several times, such as from one to five times, a day. The daily dosage regimen is selected from the range of about 10 mg to about 1.0 g, preferably 50–500 mg for oral administration and 10–250 mg for parenteral administration. When the method described above is carried out, $D_2$-agonist activity is produced.

The following examples are designed solely to illustrate the preparation and use of the compounds of this invention. The temperatures are Centigrade. Other variations of these examples will be obvious to those skilled in the art.

EXAMPLE 1

4-Hydroxyphenylacetic acid (50 g, 0.32 m) in 300 ml of glacial acetic acid was cooled to 10°, at which temperature 100 ml of nitric acid was slowly added. The mixture was allowed to reach room temperature, then was poured into 1 of water. The separated solid was washed with water and recrystallized from ethanol to give 35 g of 4-hydroxy-3-nitrophenylacetic acid, m.p. 144°–146°.

A mixture of the nitro compound and 100 ml of thionyl chloride was heated at reflux for 3.5 hours, then stripped with toluene twice to leave a solid yellow acid chloride. This was dissolved in chloroform and added dropwise to 109 ml of di-n-propylamine in 200 ml of methylene chloride. The solution was washed with 10% hydrochloric acid and water. The dried solution was stripped. The residue was recrystallized from aqueous methanol, then cyclohexane to give 30 g of N,N-di-n-propyl-3-nitro-4-hydroxyphenylacetamide, m.p. 63°–65°.

The amide (28 g, 0.1 m) was mixed with 80 ml of water/dimethylformamide, then 36 g (0.26 m) of potassium carbonate. The red mixture was maintained at 35° while 15 ml (0.16 m) of methyl sulfate was added dropwise with stirring. The reaction mixture was quenched in 250 ml of water and extracted with ethyl acetate. The extract was washed with alkali, water, acid and brine. After drying and stripping, the methyl ether product remained.

A mixture of 14.7 g (0.05 m) of this compound and 100 ml of tetrahydrofuran was stirred while 100 ml (0.1 m) of 1.0M boron hydride in tetrahydrofuran was added. The mixture was heated at reflux for 2 hours. 10% Hydrochloric acid (100 ml) was added. Refluxing was continued for 1 hour. The mixture was stripped and 100 ml of 10% hydrochloric acid added. The product was extracted into methylene chloride which was dried and stripped. The residue was placed under low reduced pressure for 2 hours to give 16 g of a yellow oil; N,N-di-n-propyl-3-nitro-4-methoxyphenethylamine hydrochloride.

The phenethyl amine (16 g, 0.05 m) was taken up in 250 ml of ethanol and hydrogenated with 0.1 g of platinum oxide at low pressure for 9 hours. The filtered reaction mixture was stripped to give 12.7 g of crude N,N-di-n-propyl-3-amino-4-methoxyphenethylamine hydrochloride. After recrystallization from isopropanol/ether, 7.5 g of white diamine, m.p. 139°–141°, was recovered.

The diamine (10 g, 0.035 m) in 100 ml of chloroform was stirred with 83.1 g (0.105 m) of phosgene overnight at room temperature. The volatiles were removed by evaporation to give 11.09 g of a tan solid, m.p. 118°–120°, which is the isocyanate intermediate.

This material was reacted with O-benzylhydroxylamine (6.38 g, 0.04 m) in chloroform at room temperature overnight. The mixture was then stripped. The residue was redissolved in chloroform and again stripped by evaporation. The residue was triturated with ether and pumped under high vacuum for 20 minutes to give 17.4 of crude yellow urea.

The yellow solid (17.4 g, 0.04 m) in 100 ml of chloroform was stirred in an ice bath while 16.9 g (0.038 m) of lead tetraacetate was added slowly. The mixture was stirred at reflux for 1.5 hours to give a semisolid which demonstrated two spots. The semisolid was separated by filtration. The product cake was washed with chloroform and, then, passed over a silica column (400 g) using chloroform/methanol eluant. The late fractions gave 5.42 g (30%) of N-benzyloxybenzimidazolone, m.p. 92°–95°, as the acetate salt.

The salt (5 g) was converted to the base with 10% sodium bicarbonate solution/chloroform. The organic extract was dried and evaporated. The base was taken into 250 ml of ethanol. An excess of Raney nickel catalyst was activated and added. The mixture was hydrogenated at moderate pressure at 50° for 18 hours. Thin layer analysis on silica demonstrated a single spot. The catalyst was removed and washed. The organic extracts were evaporated to give 2.39 g (75%) of crystalline solid 4-methoxy-7-[2-(N,N-di-n-propylamino)ethyl]-1,3-benzamidazol-2-one base.

EXAMPLE 2

A mixture of 1.83 g (0.00629 m) of 4-methoxy-7-[2-(N,N-di-n-propylamino)ethyl]-1,3-benzimidazol-2-one in 100 ml of methylene chloride was cooled to −30° while 17.5 ml of 1M boron tribromide in methylene chloride was added dropwise. After standing at room temperature for 4 hours, the mixture yielded an oil which solidified. The residue was triturated with methanol, then recrystallized from isopropanol to give 1.94 g (86%) of 4-hydroxy-7-[2-(N,N-di-n-propylamino)ethyl]-1,3-benzimidazol-2-one hydrobromide; 240°–242°.

Anal. Calcd. for $C_{15}H_{23}N_3O_2 \cdot HBr$: C, 50.28; H, 6.75; N, 11.73. Found: C, 50.22; H, 6.75; N, 11.46.

An aliquot of 100 mg of the salt was shaken in methylene chloride-10% bicarbonate. Separation, drying and evaporation of the organic layer gave the base.

EXAMPLE 3

Using the reaction sequence of Example 1 but substituting the following amines for di-n-propylamine gives the named products:

(a) n-butyl-n-propylamine gives 7-[2-(N-n-butyl-N-n-propylamino)ethyl]-4-hydroxy-1,3-benzimidazole-2-one hydrochloride;

(b) dimethylamine gives 7-[2-(N,N-dimethylamino)ethyl]-4-hydroxy-1,3-benzimidazol-2-one hydrobromide;

(c) N-methyl-phenethylamine gives 7-[2-(N-methyl-N-phenethylamino)ethyl]-4-hydroxy-1,3-benzimidazol-2-one hydrobromide;

(d) N-n-propyl-4-methoxyphenethylamine gives 7-[2-(N-4-hydroxyphenethyl-N-n-propylamino)ethyl]-4-hydroxy-1,3-benzimidazol-2-one as the base and as the methane sulfonic acid salt.

EXAMPLE 4

7-[2-(di-n-propylamino)ethyl]-4-hydroxy-1,3-benzimidazol-2-one hydrobromide (25 mg) is mixed with 200 mg of lactose and 2 mg of magnesium stearate, filled into a hard gelatin capsule which is administered orally to a hypertensive human patient from 1–4 times daily.

What is claimed is:

1. A chemical compound of the formula:

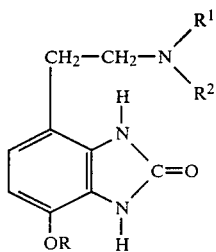

in which:

R is hydrogen or methyl; and $R^1$ and $R^2$ are, each, $C_{1-6}$-alkyl, benzyl, phenethyl, methoxyphenethyl or hydroxyphenethyl, or a pharmaceutically acceptable, acid addition salt thereof.

2. The compound of claim 1 in which $R^1$ and $R^2$ are both n-propyl or are n-propyl, 4-hydroxyphenethyl.

3. The compound of claim 1 being 7-[2-(N,N-di-n-propylamino)ethyl]-4-hydroxy-1,3-benzimidazol-2-one or a pharmaceutically acceptable acid addition salt thereof.

4. The compound of claim 1 being 7-[2-(N,N-di-n-propylamino)ethyl]-4-hydroxy-1,3-benzimidazol-2-one hydrobromide.

5. The compound of claim 1 being 7-[2-(N,N-di-n-propylamino)ethyl]-4-hydroxy-1,3-benzimidazol-2-one as the base.

6. The compound of claim 1 being 7-[2-(N-n-propyl-N-4-hydroxyphenethylamino)ethyl]-4-hydroxy-1,3-benzamidazol-2-one or a pharmaceutically acceptable acid addition salt thereof.

7. A pharmaceutical composition having $D_2$-agonistic activity comprising an effective therefor but nontoxic quantity of a compound of claim 1 combined with a pharmaceutical carrier.

8. The composition of claim 7 in which the composition is for oral or parenteral administration and is effective for treatment of hypertension.

9. The method of inducing $D_2$-agonistic activity in a patient in need thereof comprising administering internally to said patient a $D_2$-agonistic, nontoxic quantity of a compound of claim 1.

10. The method of claim 9 in which the patient is hypertensive and the administration is oral or parenteral.

* * * * *